US007988989B2

(12) United States Patent
Bedding et al.

(10) Patent No.: US 7,988,989 B2
(45) Date of Patent: Aug. 2, 2011

(54) NUTRITIONAL PRODUCT FOR ENHANCING GROWTH AND/OR STRENGTHENING THE IMMUNE SYSTEM OF EQUINE FOALS

(75) Inventors: Peter M. J. Bedding, Crediton (GB); Franklin L. Pellegrini, Streetsboro, OH (US)

(73) Assignee: Freedom Health, LLC, Aurora, OH (US)

( * ) Notice: Subject to any disclaimer, the term of this patent is extended or adjusted under 35 U.S.C. 154(b) by 1668 days.

(21) Appl. No.: 10/802,342

(22) Filed: Mar. 17, 2004

(65) Prior Publication Data

US 2005/0008679 A1 Jan. 13, 2005

Related U.S. Application Data

(63) Continuation-in-part of application No. 10/435,367, filed on May 9, 2003, now Pat. No. 7,824,706.

(51) Int. Cl.
*A61K 47/00* (2006.01)
*A61K 9/68* (2006.01)
*A61K 9/28* (2006.01)
*A23K 1/17* (2006.01)
*A23K 1/18* (2006.01)
*A23K 1/165* (2006.01)
*A23K 1/00* (2006.01)
*A23L 1/20* (2006.01)
*A23D 7/00* (2006.01)

(52) U.S. Cl. ........ 424/439; 424/438; 424/442; 424/441; 424/440; 426/630; 426/635; 426/601; 426/807

(58) Field of Classification Search .................. 424/438, 424/439, 441, 422
See application file for complete search history.

(56) References Cited

U.S. PATENT DOCUMENTS

| 4,053,492 | A | * | 10/1977 | Brooke et al. .................. 554/11 |
| 4,729,896 | A | | 3/1988 | Sawhill |
| 4,820,731 | A | | 4/1989 | Mascioli et al. |
| 4,950,656 | A | | 8/1990 | Lichtenberger |
| 5,312,636 | A | * | 5/1994 | Myllymaki et al. .......... 426/417 |
| 5,320,846 | A | | 6/1994 | Bistrian et al. |
| 5,505,968 | A | | 4/1996 | Schaefer et al. |
| 5,589,186 | A | | 12/1996 | Isobe et al. |

(Continued)

FOREIGN PATENT DOCUMENTS

JP 50-5568 5/1973

(Continued)

OTHER PUBLICATIONS

Equilibra 500 product information, 1989.

(Continued)

*Primary Examiner* — Isis Ghali
(74) *Attorney, Agent, or Firm* — Reinhart Boerner Van Deuren s.c.

(57) ABSTRACT

A novel nutritional product and methods for the manufacture and administration of the same are disclosed for the feeding of equine foals and other animals. The nutritional product of the present invention is effective in supporting the growth and health of equine foals, and in supporting and stimulating its immune system as well. The nutritional product of the present invention consists of safe and natural ingredients rather than drugs, and is orally administrable. The ingredients of the nutritional product of the present invention when combined provide a synergistic efficacy which greatly exceeds the sum of the efficacies of the individual ingredients, making the nutritional product highly effective in promoting and enhancing the growth, nutritional uptake, and immune system of equine foals.

35 Claims, 1 Drawing Sheet

U.S. PATENT DOCUMENTS

| | | | |
|---|---|---|---|
| 5,660,852 | A | 8/1997 | McKeown et al. |
| 5,716,639 | A | 2/1998 | Carlsson et al. |
| 5,759,537 | A | 6/1998 | Garnett |
| 5,972,985 | A | 10/1999 | Thomas et al. |
| 6,019,995 | A | 2/2000 | Steensma |
| 6,020,324 | A | 2/2000 | James et al. |
| 6,045,834 | A | 4/2000 | Howes et al. |
| 6,096,870 | A | 8/2000 | Mozaffar et al. ............ 530/366 |
| 6,117,458 | A | 9/2000 | Morgan |
| 6,156,355 | A | 12/2000 | Shields et al. |
| 6,200,624 | B1 | 3/2001 | Mazer et al. |
| 6,203,818 | B1 | 3/2001 | Vester |
| 6,329,414 | B1 | 12/2001 | Thomas et al. |
| 6,344,221 | B1 | 2/2002 | Evans |
| 6,355,693 | B1 | 3/2002 | Herslof et al. |
| 6,410,067 | B1 | 6/2002 | Kanter et al. ............... 426/272 |
| 6,451,370 | B1 | 9/2002 | Anderson |
| 6,537,544 | B1 | 3/2003 | Johansson et al. |
| 6,759,064 | B2 | 7/2004 | Morré et al. |
| 2002/0044988 | A1 | 4/2002 | Fuchs et al. |
| 2003/0153746 | A1* | 8/2003 | Van Lengerich et al. ....................... 536/123.12 |
| 2003/0165604 | A1 | 9/2003 | Tsubaki et al. |

FOREIGN PATENT DOCUMENTS

| | | |
|---|---|---|
| JP | 09-262061 | 10/1997 |
| JP | 2004051582 | 2/2004 |
| WO | 9839980 | 9/1998 |
| WO | 9901044 | 1/1999 |
| WO | WO99/18188 | 4/1999 |
| WO | 9953772 | 10/1999 |
| WO | WO 0117366 | 3/2001 |
| WO | WO 0174173 | 10/2001 |
| WO | WO 2005002367 | 1/2005 |

OTHER PUBLICATIONS

"Arteriovenous difference for glutamine in equine gastrointestinal tract" by Duckworth et al. AM J Vet Res, vol. 53, No. 10, Oct. 1992.
"Effect of varying content of soluble dietary fibre from wheat flour and oat milling fractions on gastric emptying in pigs" by Johansen et al.; British Journal of nurtition (1996), 75, 339-351.*
Hallfrisch et al. "Diet containing soluble oat extracts improve glucose and insulin responses of moderately hypercholesterolemic men and women", Am J Cln Nutr, 1995;61:397-84.*
Bengmark et al. "Gastroinstestinal surface protection and mucosa reconditioning"; JPEN J Partenter Enteral Nutr. Sep.-Oct. 1995; 19(5) : 410-5.*
Soybean~the golden nugget Ishi Khesla Posted online: Sat. Apr. 22, 2006.*
PFNDAI, Mar. 2005, Badami et al.*
"Barley Beta Glucans Application in Obesity", Peter M. Schkoda, supplement to AgroFOOD industry hi-tech, Sep./Oct. 2008, vol. 19, No. 5.*
"Optimizing Cardio Health With Oat Beta-Glucans", Gregory Stephens, Functional Ingredients Magazine, Apr. 1, 2005.*
Winawer, Neil M.D.; Williams, Mark V., M.D.; Making Health Care Safer: A Critical Analysis of Patient Safety Practices; Chapter 33, University of California at San Francisco (UCSF)—Stanford University Evidence-based Practice Center, AHRQ Publication 01-E058, Jul. 20, 2001.
"β-Glucan", website at www.lsbu.ac.uk/water/hygly, pp. 1-2.
"Frequently Asked Questions About Beta Glucan 1, 3 D Glucan", About betaglucan.com website, pp. 1-4.
"Strengthening My Immune System With Beta Glucan", About betaglucan.com website, pp. 1-5.
"Gastric Ulcers in Horses: A Widespread but Manageable Disease", www.equinecentre.com.au/health_diseases_ulcers.shtml, pp. 1-4.
"Triple Crown Horse Feeds: Equimix Technology", www.triplecrownfeed.com/equimixtech.php, pp. 1-4.
"Ultra Mannan Oligosaccharide", www.ultrateck.net/petfood/yeasts.html, pp. 1-2.
"DevRx Laboratories, Inc. makes horses healthier with BioEquine™!" horses.about.com/cs/news/a/bioequine1592.html.

Miller, Alan L., ND, "Therapeutic Considerations of L-Glutamine: A Review of Literature", www.thorne.com/altmedrev/fulltext/glutamine4-4.html, Dec. 2002, pp. 1-12.
"Power Plus™ L-Glutamine: Body Builders Love Our L-Glutamine" www.pricespower.com/Iglutamine, pp. 1-6.
"A Bit About Our Products: Hyaluronic Acids", www.kemme.ca/prodmain.html, pp. 1-4.
"DrHormone.com—Vitamins and Supplements", www.schwarzbeinprinciple.com/pgs/vitamins_01.html, pp. 1-5.
"Single Amino Acids", www.intensivenutrition.com/SingleAminoAcids.htm, pp. 1-5.
"Solgar Amino Acids", www.allabout-solgar-vitamins.com/solgar-amino-acids.html, pp. 1-4.
Briggs, Karen, "Provided By: The Horse Interactive Malicious Mycotoxins", www.thehorse.com/print.asp?fid=3695, pp. 1-4.
"Frequently Asked Questions: How Common is EGUS?", gastrogard.us.merial.com/faq.asp, pp. 1-4.
"Sites of Drug Action", www.egus.org/vet/treatment4.htm, pp. 1-3.
"The Truth: About Beta Glucan Products", www.beta-glucan-13d.com, pp. 1-4.
Lanigan, A.J., "Uptake Mechanism of Beta Glucan", www.Beta-glucan-13d.com/beta-glucan-mechanism.htm, pp. 102.
"Beta Glucan Research—*Saccharomyces cerevisiae*", ww.betaglucan.org, pp. 1-7.
"β-glucan", www.ceapro.com/_pages/Beta_glucan.htm, one page.
"Phospholipids", users,rcn.com/jkimball.ma.ultranet/BiologyPages/P/Phospholipids.html, one page.
"Oligosaccharide", encarta.msn.com/encnet/features/dictionary/DictionaryResults.aspx?refid=1861634848, one page.
"Re: ProfHeath—membrane synthesis", 216.239.33.100/search?q=cache:H3_DvEn0rMEC:www.cquest.utoronto.ca/botany/bio250y/talk/lectures/lec3/messages.html, one page.
Russett, Dr. J.D., "Specialty Products Research Notes: Lecithin and Equine Ulcers", Central Soya, LEC-H-55, Mar. 2002, pp. 1-10.
"L-Threonine", www.ajinomoto.co.jp/ajinomoto/A-Life/e_aminoscience/bc/amino_16.html, one page.
Adams, Dr. Clifford A., "What are Nutricines?", www.eclecticcooking.com/WhatAreNutricines.htm, pp. 1-2.
Lardy, Greg, Poland, Chip, "Feeding Management for Horse Owners", AS-953, www.ext.nodak.edu/extpubs/ansci/horse/as953w.htm, Feb. 2001, pp. 1-6.
"Mycosorb", translate.google.com/translate?hl=en&sl=pt&u=http://www.va-industria.pt/support.html&prev=/search%3Fq%3Dmycosorb%26hl%3Den%26, one page.
"Alltech to Exhibit Range of Natural Products at Space 2002", www.alltech-bio.com/alltech%5Calltech2.nsf/pages/News_Alltech_to_Exhibit_Range_of_Natural_Products_at_Space_2002, one page.
"Unraveling the Mystery of Mycotoxins", www.alltech-bio.com/alltech%5Calltech2.nsf/pages/News_UNRAVELLING_THE_MYSTERY_OF_MYCOTOXINS, one page.
"Consistent Responses Confirm Bio-Mos Efficacy", www.alltech-bio.com/alltech%5Calltech2.nsf/pages/News_CONSISTENT_RESPONSES_CONFIRM_BIO-MOS_EFFICACY, one page.
"L-Glutamine Side Effects and Benefits", www.bodybuildingforyou.com/supplements-reviews/glutamine-side-effects-benefits.htm, pp. 1-2.
Miller, Alan L. M.D., "Therapeutic Considerations of L-Glutamine: A Review of the Literature", pp. 1-11.
Reynolds, Judith A., Ph.D, P.A.S., "Are You Feeding Your Horse Like a Horse", Moorman's Feed Facts, Oct. 2000, pp. 1-4.
Bekers M et al: "Oats and fat-free milk based functional food product" Food Biotechnology, Dekker, New York, NY, US, 15(1), 1-12 (2001).
McClure SR, Glickman LT, Glickman NW. Prevalence of gastric ulcers in show horses. J Am Vet Med Assoc 1999;215: 1130-1133.
Traub-Dargatz JL, Kopral CA, Seitzinger AH, Garber LP, Forde K, White NA. Estimate of the national incidence of and operation-level risk factors for colic among horses in the United States, spring 1998 to spring 1999. J Am Vet Med Assoc. Jul. 1, 2001;219(1):67-71.
Lorenzo-Figueras M, Merritt AM. Effects of exercise on gastric volume and pH in the proximal portion of the stomach of horses. An J Vet Res. 2002;63:1481-1487.

Mair, Tim, Tom Divers, and Norm Ducharme. Manual of Equine Gastroenterology. London: WB Saunders, 2002.

Mitchell RD. Prevalence of Gastric Ulcers in Hunter/Jumper and Dressage Horses Evaluated for Poor Performance. Assoc. Equine Sports Med., Sep. 2001.

Kronfeld DS. Speed Limit. Dipl. ACVN, Dipl. ACVIM. Mar. 2003 Article # 4212.

Pellegrini, Frank. A Large-scale Necroscopy of Equine Ulcers. Submitted to Equine Veterinary Journal, 2004.

Martin GP, Marriott C, Kellaway IW. The interaction of progesterone with mucus glycoproteins. Pharm Acta Helv. 1981;56(1):5-8.

Kiviluoto T, Paimela H, Mustonen H, Kivilaakso E. Exogenous surface-active Phospholipids protects Necturas gastric mucosa against luminal acid and barrier-breaking agents. Gastroenterology. Jan. 1991; 100(1):38-46.

McNeil PL, Ito S. Gastrointestinal cell plasma membrane wounding and resealing in vivo. Gastroenterology. May 1989; 96(5 Pt 1): 1238-48.

Dupree JL, Coetzee T , Blight A, Suzuki K, Popko B (1998), Myelin galactolipids are essential for proper node of Ranvier formation in the CNS. J Neurosci 18(5):1642-49.

Kreitler B. Feed and Nutrition: Fat: The Next Nutraceutical? Thoroughbred Times, Apr. 12, 2003.

Davidson MH, Dugan LD, Bums JH, et al. The hypocholesterolemic effects of betaglucan in oatmeal and oat bran. A dose-controlled study. JAMA 1991;265:1833-9.

Bell S , Goldman VM, Bistrian BR, et al. Effect of beta-glucan from oats and yeast on serum lipids. Crit Rev Food Sci Nutr 1999;39:189-202 [review].

Braaten JT, Scott FW, Wood PJ, et al. High beta-glucan oat bran and oat gum reduce postprandial blood glucose and insulin in subjects with and without type 2 diabetes. Diabet Med 1994; 11:312-8.

Tappy LE, Gugolz E, et al. Effects of breakfast cereals containing various amounts of beta-glucan fibers on plasma glucose and insulin responses in NIDDM subjects. Diabetes Care 19(8):831-4. Aug. 1996.

Czop JK. The role of beta-glucan receptors on blood and tissue leukocytes in phagocytosis and metabolic activation. Pathol Immunopahtol Res 1985;5:286-96. 1986.

Estrada A, Yun CH, Van Kessel A, et al. Immunomodulatory activities of oat beta-glucan in vitro and in vivo. Microbiol Immunol 1997;41:99 1-8.

Reid DM, Montoya M, et al. Expression of the beta-glucan receptor; Dectin-1, on murine leukocytes in situ correlates with its function in pathogen recognition and reveals potential roles in leukocyte interactions. J Leukoc Biol 76(1):86-94. Jul. 2004.

Bolm N, Kulicke W. Rlzeological studies of barley (1-3)(1-4) beta-glucan in Concentrated solution, Carbohydrate Research, 1999, 315, 293-301.

Wursch P, Sunyer FX. The role of viscous soluble fiber in the metabolic control of diabetes. A review with special emphasis on cereals rich in beta-glucan. Diabetes Care 20(11):1774-80. 1997.

Roth E, Spittler A, Oehler . Glutamine: effects on the immune system, protein balance and intestinal functions. Wien Klin Wochenshr. 1996;108(21):667-8.

Duckworth DH, Madison JB, et al. Arteriovenous differences for glutamine in the equine gastrointestinal tract. Am J Vet Res 53(10):1864-7. Oct. 1992.

Vazquez P, Gomez de Segura IA, Cos A, Candela CG, De Miguel E. Response of the intestinal mucosa to different enteral diets in situations of surgical stress and malnutrition. Nutr Hosp. Nov.-Dec. 1996; 11(6):321-7.

Bertolo RF, Chen CZ, Law G, Pencharz PB, Ball RO. Threonine requirement of neonatal piglets receiving total parenteral nutrition is considerably lower than that of piglets receiving an identical diet intragastrically. J Nutr. Oct. 1998; 128(10):1752-9.

Ball RO, Law G, Bertolo RFP, Pencharz PB. Adequate oral threonine is critical for mucin production and mucosal growth by neonatal piglet gut. Proceedings of the VIllth International Symposium on Protein Metabolism and Nutrition, EAAP, 1999.

Cuaron JA, Chapple RP, Easter RA. Effect of lysine and threonine supplementation of Sorghum in gestation diets on nitrogen balance and plasma constituents in first litter gilts. J. Anim. Sci., 58, 631-637 Mar. 1984.

Bueno J, Torres A, Almendros A, Carmona R, Nunez MC and Gil A, (1994) Effect of dietary nucleotides on small intestinal repair after diarrhea. Histological and ultrastructural changes. Gut 35:926-933.

Uauy R, Stringel G, Thomas R and Quan R, (1990) Effect of dietary nucleosides on growth and maturation of the developing gut in the rat. J. Pediatr. Gastroenteral. Nutr. 10:497-503.

Marshman E., Booth C., Potten CS., The intestinal epithelial stem cell. Bioessays Jan. 2002; 24(1):91-8.

Lin, Cheng-mao. Effect of Dietary Nucleotide Supplementation on In Vivo and In Vitro Immune Function in Protein-Malnourished Mice. University of Florida. PhD. Dissertation. Dec. 1995.

Ip WK, Lau YL. Role of mannose-binding lectin in the innate defense against *Candida albicans*: enhancement of complement activation, but lack of opsonic function, in phagocytosis by human dendritic cells. J Infect Dis Aug. 1, 2004;190(3):632-40. Epub Jun. 28, 2004.

Swanson KS, Grieshop CM, Flickinger EA, Healy HP, Dawson KA, Merchen NR, Fahey GC Jr. Effects of supplemental fructooligosaccharides plus mannanoligosaccharides on immune function and ileal and fecal microbial populations in adult dogs. Arch Tierernahr. Aug. 2002;56(4):309-18.

Bland EJ, Keshavarz T, Buclte C. The influence of small oligosaccharides on the immune system. Carbohydrate Research, vol. 339, issue 10. 2004.

Newman, K. 1994. Mannan-oligosaccharides: Natural polymers with significant impact on the gastrointestinal microflora and the immune system. Biotechnology in the Feed Industry, Nottingham University Press, Nottingham, UK, pp. 167-174.

Davis E., Maxwell C., Kegley B., de Rodas B., Friesen K and Hellwig D., Efficacy of Mannan Oligosaccharide (Bio-Mos) Addition at Two Levels of Supplemental Copper on Performance and Immunocompetence of Early Weaned Pigs. Arkansas Animal Science Department Report 1999.

\* cited by examiner

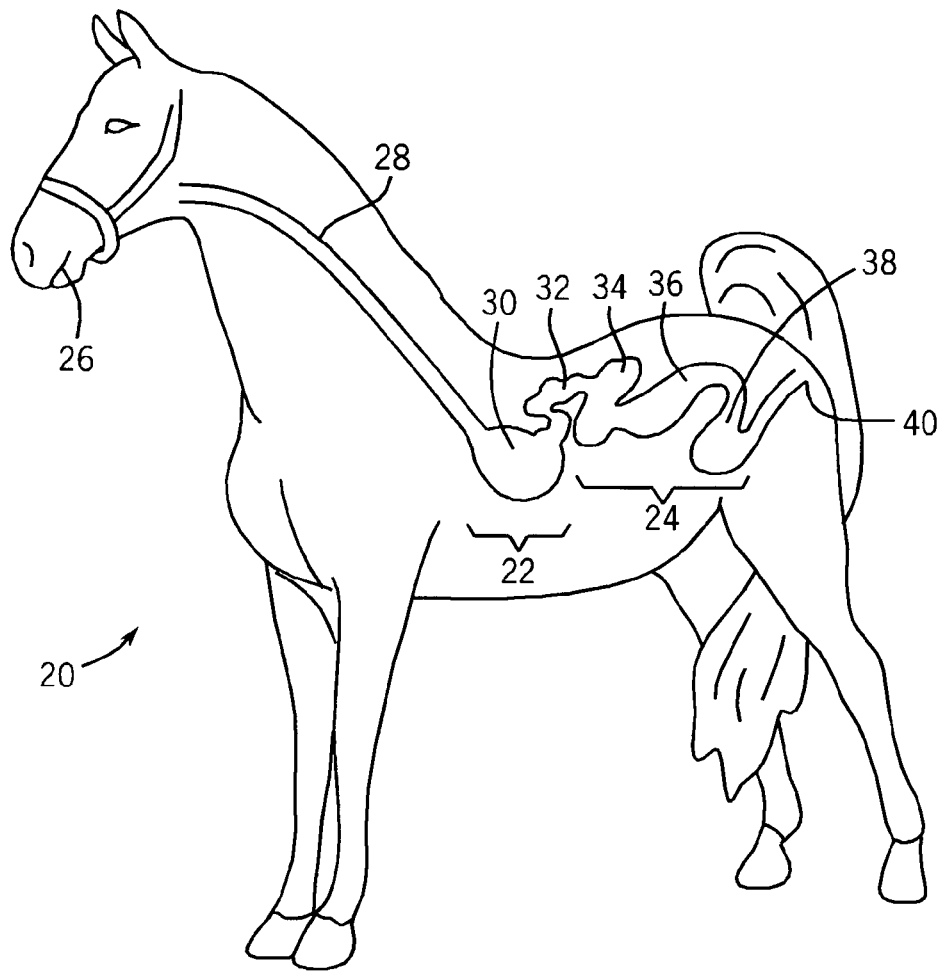
FIG.

NUTRITIONAL PRODUCT FOR ENHANCING GROWTH AND/OR STRENGTHENING THE IMMUNE SYSTEM OF EQUINE FOALS

IDENTIFICATION OF RELATED APPLICATIONS

This patent application is a continuation-in-part of U.S. patent application Ser. No. 10/435,367, filed on May 9, 2003, now U.S. Pat. No. 7,824,706 entitled "Dietary Supplement and Method for the Treatment and Prevention of Digestive Tract Ulcers in Equines and Other Animals," which patent application is assigned to the assignee of the present invention, and which patent application is hereby incorporated herein by reference in its entirety.

BACKGROUND OF THE INVENTION

Field of the Invention

The present invention relates generally to nutritional product for horses and other animals, and more particularly to a novel nutritional product for use to optimize the nutritional requirements for an equine foal or other animal from the neonatal stage to the yearling stage.

As with any young mammal, the equine foal has special nutritional requirements which are required in order to optimize its health and growth rate. This is particularly the case if the foal is intended to become a performance horse, either a racehorse or a show horse. While genetics and environmental conditions undoubtedly play a significant role in the growth and development in determining the growth potential of each foal, nutrition must also be taken into account and is certainly of vital importance in the health, growth, and development of foals and young horses.

As such, feeding the foal and the young horse, particularly in conjunction with the variables associated with a lactating mare, is a matter requiring careful balance which must be taken seriously. The interaction of genetics, environment, management, and nutrition of the foal and the mare is quite complex. It has been determined that the nutrition which a foal receives initially will have a profound and long-term effect on the health, development, and soundness of the foal for its entire lifetime. It is of primary importance that the diet of a foal be the focus of a balanced dietary approach and that the provision of essential ingredients in its diet support the health and the growth of the foal.

Under normal conditions, the mare will hopefully produce enough milk for the foal, typically about fifteen liters per day. While this should provide sufficient nutrition for the foal to develop, there are a number of factors that can disturb the balance and result in the foal receiving insufficient nutrition to grow and develop properly. It is essential that the foal ingest "first milk" or colostrum which is produced by the mare for the first several days after giving birth and which provides the foal with the important immunoglobulin and antibodies which enable it to resist infections and which protect it from a variety of diseases. This ingestion of colostrum is called "passive transfer."

Upon ingestion of the colostrum by the foal, the special cell tissue which are contained in its intestinal mucosa will absorb and transmit the immunoglobulin and antibodies contained in the colostrum into the blood of the foal. Since these cells in the foal's intestinal mucosa are typically replaced within the first thirty-six hours of life, it is essential that the foal is suckling within the first six to eight hours of its life, which is the time that the antibodies reach the peak level of absorption in the gastrointestinal tract of the foal. It is preferable that the foal is suckling within two to three hours of its birth to be absolutely certain of antibody absorption, and it is a general principle that the earlier a foal suckles, the more antibodies it will receive.

There are a number of factors which can cause either a reduced level of passive transfer or a failure of passive transfer. These factors include poor colostral quality (insufficient immunoglobulin and antibodies contained in the colostrum, early production of colostrum by the mare prior to foaling, low milk yield (which may be due to the mare losing her milk), low antibody transfer as a result of poor feeding by the foal (sometimes due the mare refusing to allow the foal to suckle), malabsorption by the intestinal mucosa of the foal, and premature birth of the foal resulting in insufficient production of colostrum. Additionally, on the ninth day after birth, the mare goes into heat and foals are likely to get diarrhea at this time.

A foal's immune system is built up from the time of its birth, first due to the initial colostrum provided by the mare and later from environmental conditions. The immunity resulting from the immunoglobulin and the first antibodies are the most important immunity that a foal must acquire. During the early days of a foal's life, it will be invaded by bacteria, some of which are beneficial and will help in digestion, others of which are pathogens that will attempt to survive and produce toxins in the foal's body or cause diseases. During this time, the foal must begin to produce its own immunity defenses, and special cells will begin to be produced and to circulate in the blood to protect the foal's body from this invasion of pathogens.

In order to understand the next aspect of a foal's proper nutritional development, it is necessary to understand the basic principles of the digestive system of horses. While horses are monogastric (one stomach) animals, they are also hindgut fermenters, which means that they have relatively small stomachs and small intestines (collectively referred to as the foregut), and relatively large colons (collectively referred to as the hindgut). The relative volume of the foregut in horses is approximately thirty-five to forty percent of the total volume of the digestive tract. By comparison, the relative volume of the foregut in pigs is sixty to sixty-five percent of the total volume of the digestive tract, and the relative volume of the foregut in ruminant animals such as cows is eighty-five to ninety percent of the total volume of the digestive tract.

While the foregut of horses is relatively small, their stomachs are even smaller, representing only approximately one-quarter of the volume of the foregut, and thus approximately nine percent of the total volume of the digestive tract. In view of the small percentage of the digestive tract represented by the stomach, one might refer to a horse's stomach as a preparatory chamber. The principal consequence of this relatively small stomach size is that the rate of passage of feed through horses' stomachs is relatively fast, leaving relatively little time for the digestion process to occur. In addition, smaller feed particles pass through horses' foreguts even more quickly, with the time of passage of such smaller particles through the horses' stomachs potentially not allowing for proper digestion to occur.

The mare will pass on beneficial bacteria in her feces that the foal will nibble at and ingest, and these bacteria provide the foundation for the foal's own beneficial microflora. Under optimum conditions, these bacteria will flourish, and will enable the foal to begin to use its hindgut and eventually to become a full-fledged hindgut fermenter. This process takes many months, and will not be complete until the foal is at least a year old, at which time it has become a fully efficient hindgut fermenter.

During the first six months of this period, it is desirable that the mare's diet be controlled, and that the mare's own hindgut microflora are looked after and that any pathogens or mycotoxins that are ingested are not allowed to proliferate or enter the mare's blood stream and affect milk quality or quantity. These pathogens and mycotoxins should not be allowed to be passed over to the foal. As such, functional feeding of both the mare and the foal is important, and will help support the beneficial microflora in their respective hindguts.

Prior to completing this discussion about a foal's initial digestive system development, it is beneficial to discuss a consequence of the somewhat unique digestive tract anatomy of horses, namely a high incidence of digestive tract ulcers in horses. In the case of humans and most other animals, gastric acid is secreted in the stomach in response to eating. In contrast, horses have developed over millennia as trickle feeders (eating slowly but more or less continuously over most of the day), and their digestive systems are geared for such a diet, with a continuous production of gastric juices and bile secretion into the foregut from the liver. Thus, the stomach of a horse may be thought of as an acid pump that produces gastric acid more or less continuously through the day, whether or not the horse is being fed.

The incidence of digestive tract ulcers in performance horses has risen most sharply, from approximately twenty percent in 1920 to approximately ninety percent or better in the last decade. In racehorses, for example, as much as ninety-seven percent of the racehorse population has been reported to have digestive tract ulcers, with the percentage of show horses having digestive tract ulcers lagging only slightly behind. Even performance horse foals have been inflicted with this condition, with approximately sixty percent of performance horse foals having digestive tract ulcers. While pleasure horses have a lower incidence of digestive tract ulcers than show horses, the increasing incidence of digestive tract ulcers in the last two decades has been significant for all segments of the horse population, including pleasure horses.

A recent scientific study of a random cross-section of horses indicated that approximately fifty-five percent of them had gastric ulcers and forty percent of them had colonic ulcers. The incidences of gastric and colonic ulcers were not identical, meaning that some horses had only gastric ulcers and other horses had only colonic ulcers. However, a large percentage of the horses that had colonic ulcers also had gastric ulcers, with less than thirty percent of the horse population as a whole not having either gastric or colonic ulcers. As mentioned above, the incidence of digestive tract ulcers for show horses and racehorses is even higher than these statistics for the general horse population.

The direct cause of digestive tract ulcers in horses appears to be excess stomach acid, as is the case with humans and other animals. Excess stomach acid can "eat" through the protective lining of the stomach and damage the interior surface of the stomach, causing gastric ulcers. In humans, it is believed that the prevalent factor in the development of stomach ulcers is the *helicobacter pylori* bacteria. However, the *helicobacter pylori* bacteria has not been isolated from horse stomachs, and thus is not believed to be a factor in the development of digestive tract ulcers in horses.

The inside wall of the stomach is protected by a mucous gut membrane lining which is a fatty layer containing polar lipids. When there is no food contained in the horse's stomach, the gastric acid will act on the mucous gut membrane lining the inside wall of the stomach, oxidizing the cells of the gut lining and burning them up. These burned-up gut lining cells are sloughed off, and pass through the digestive system, exposing the gut wall to the gastric acid and allowing gastric ulcers to form. This condition is known as equine gastric ulcer syndrome ("EGUS").

In addition, there is a continuous peroxidation and oxidation of proteins and lipids which results in the formation of free radicals. As the fatty cells containing polar lipids in the mucous gut membrane are oxidized and burned off, free radicals are created. These free radicals can break down muscle tissue, and have been shown to have an adverse affect on the performance of horses. Thus, it is readily apparent to those skilled in the art that digestive tract ulcers have a substantial adverse effect on performance horses, and can prevent performance horses from achieving their true potential.

In the case of humans, the production of saliva and its mixing with ingested foodstuffs initiates the digestion process since human saliva includes the enzyme amylase, which breaks down starch into sugar. Horse saliva does not contain amylase or any other enzyme that can initiate the digestion process. However, horse saliva does contain a buffering agent that can help to neutralize gastric acid contained in the horse's stomach.

Another unique feature of horses' digestive tracts is the presence of a large microbial population in the hindgut. These microorganisms are responsible for the fermentation of the residues of the digestive process and absorption of digested feed, and have the ability to utilize the cellulose that is present in forages. The anatomy of the hindgut, which has a number of folds contained therein, causes the passage of ingested feed to pass through relatively slowly as compared to the rate of passage of ingested feed through the foregut. While this is advantageous when digesting roughages such as forage, it can also predispose a horse to digestive upsets when insufficient roughage is contained in the ingested feed.

In addition to the unique anatomy of horses' digestive tracts, there are several other factors which also appear to increase the incidence of digestive tract ulcers in horses. These factors include feeding practices, physical stress (including the stress from being in a stable as much as twenty-three hours of the day), and medications being given to the horses. In the case of performance horses, two additional factors which can also increase the incidence of digestive tract ulcers are the intensity of training and the initiation of training of foals at a young age, the latter of which is particularly prevalent with racehorses. However, it has been determined by the inventors that while all of these factors are significant, the primary factors are the unique physiology of the horse digestive tract and modern feeding practices, with the other factors acting to further exacerbate a condition which is essentially caused by two aforesaid primary factors.

Thus, other than the unique physiology of horses' digestive tracts, the primary factor leading to the high incidence of digestive tract ulcers in horses is diet-related, and is a consequence of a drastic change in the diet of most horses. Until the relatively recent past, horses for the most part had been allowed to be free-range grazers, with a diet that consisted primarily of forage. However, beginning in the 1920's, fewer and fewer horses have had the opportunity to free range graze, or even to have the freedom to eat hay or other forage during much of the day. Instead, most horses are fed diets that are high in grains, with forage either being reduced to minimal levels or eliminated entirely from the horses' diets. Typical feeding schedules for horses are twice or three times daily, generally with feedings in the morning and the evening, and a third feeding at midday, mimicking a human diet. With this change in diet, the incidence of digestive tract ulcers in horses has increased tremendously, especially in performance horses (including both racehorses and show horses), which also have additional stresses that exacerbate the problem caused by the consequences of a low forage diet and the nature of the digestive tract of horses.

When horses are allowed to eat forage (which is essentially high fiber, low nutrition material), as they have evolved to do, they typically eat for approximately sixteen hours a day. If allowed to graze, they will begin feeding in the early morning, and will continue to feed until well after dark, nibbling, chewing, swallowing, and digesting slowly to keep their small stomachs from becoming empty. Given free choice, horses will search out and find a balanced diet typically consisting of grasses, berries, and leaves, which provide a balance of essential microminerals in addition to basic volume and energy requirements. The constant chewing produces saliva that neutralizes the gastric acid. (Saliva contains positive ions ("cations") which counteract the negative ions ("anions") of gastric acid.)

Most horses today are neither kept in pastures where they can eat forage all day long, nor fed forage in a stable. Instead, stabled horses are typically fed a concentrated, low volume diet of grain products with relatively small quantities of hay or forage being available to them, and then only intermittently. With regard to racehorses and other performance horses, the diet bears even less resemblance to a forage diet. Racehorses are fed a high-energy diet to maximize muscle growth and activity levels; this diet typically consists of a mixture of grains, molasses, nutrients, and feed additives, usually with minimal hay in the form of one or two flakes with each meal.

The concentrated, low volume diet of grain products is generally fed to the horses three times (or in some cases only twice) a day, and the horses generally eat it rapidly. When fed to horses, such a low volume diet of grain products passes through their stomachs relatively quickly. Since this type of diet is concentrated and of high quality, horses fed such a diet are not nutritionally underfed; rather, they are "behaviorally" underfed. Diets that are low in fiber and high in starch increase the potential that starches which are not digested in the foregut will enter the hindgut, where they will rapidly ferment, causing a rapid reduction in the pH level in the hindgut and a volatile fatty acid imbalance. The acidic environment created in this manner has a direct effect on the balance of microflora (the huge community of microorganisms which forms a complex and dynamic ecosystem within the hindgut) within the hindgut.

One consequence of such a diet is that relatively little of the buffering saliva reaches the horses' stomachs. This is due to the fact that the buffering capacity is determined mainly by the volume of saliva that is produced while horses are eating. For a given weight of concentrated food such as grain products, the volume of saliva produced is less than half the volume of saliva that would be produced by the same weight of forage. Thus, it will at once be appreciated by those skilled in the art that, except for the relatively brief time when horses are eating and shortly thereafter, their stomachs will be empty, with no buffering saliva. Since horses' stomachs are not adapted to such intermittent feeding, they will constantly be bathed with gastric acid, causing gastric ulcers.

Since the gastric acid from the stomach can flow into the hindgut, it is also possible for horses to have colonic ulcers, particularly ulcers in the large intestine, typically in the right ventral colon. The consequences of colonic ulcers in horses are caused or exacerbated due to the presence of pathogens and mycotoxins in the hindgut. These pathogens and mycotoxins can fasten themselves onto the lesions and cause infections in the walls of the hindgut. The pathogens and mycotoxins are ingested by horses in their feed, and are metabolites of funguses growing on the feed. Generally, the pathogens and mycotoxins will pass through horses' digestive tracts unless there are colonic ulcers that are susceptible to the pathogens and mycotoxins. Pathogens and mycotoxins can cause severe problems including digestive, reproductive, neurological, and athletic problems, as well as chronic obstructive pulmonary disease ("COPD") in horses. For example, colonization on sites of colonic ulcers caused by pH changes and attack by acids can cause transit of mycotoxins into the blood, and eventually may result in damage to the liver and even renal dysfunctions.

There are three solutions to the problem of digestive tract ulcers in horses that have been utilized in the art, none of which have been satisfactory. The first known solution is the use of antacids, also referred to euphemistically as "gastric ulcer transnutrients." Antacids (typically mixtures of magnesium and aluminum hydroxide) are administered to temporarily neutralize acid in the stomach. However, antacids are treating the symptom rather than the problem, and are relatively ineffective due to the fact that they pass rapidly through horses' stomachs, and thus an increase in pH in the stomach that is achieved with antacids is typically of short duration. In addition, since gastric acid is constantly produced by horses, it will at once be appreciated by those skilled in the art that antacids are substantially ineffective in treating digestive tract ulcers in horses.

The second known solution is the use of drugs, which are administered to inhibit the production of gastric acid. These are presently three classes of drugs which are used for this purpose: histamine type-2 antagonists such as cimetidine (available from GlaxoSmithKline under its registered trademark TAGAMET) and ranitidine (available from Pfizer under its registered trademark ZANTAC or from Ranvet under its registered trademark ULCERGUARD), or proton pump inhibitors such as omeprazole (available from Astra AB under its registered trademark GASTROGARD). These drugs claim to be effective in curing gastric ulcers in three to four weeks, but are very expensive. It is apparent to those skilled in the art that the temporary change in the stomach environment is highly unlikely to result in complete restoration of health during treatment.

They do have several disadvantages in addition to their expense, the most problematic of which is that once they are discontinued the digestive tract ulcers will usually recur quickly, requiring another round of treatment. In some instances, veterinarians may find it necessary to prescribe continuing treatment with one of these medications, which becomes extremely expensive. In addition, some of these drugs must be withheld prior to racing in the case of racehorses. Another profound disadvantage is that these drugs interfere with proper digestion by changing the natural pH balance, which results in the treated horses being in less than optimum condition.

The third, and most effective, known solution is the only natural solution known at present—rest and a diet of forage. This means allowing horses to return to pasture, and a diet of hay and other forage. It is the only real solution that has been known in the art, and it is the universal prescription to provide a complete return to health. For performance horses, it may inhibit the ability of the horses to compete; for owners of other horses it represents an ideal solution that is simply not possible. Accordingly, rest and diet does not represent an optimal solution for many horses and their owners.

Returning now to the discussion of foal nutritional system development, a foal significantly changes its suckling habits about ten days to two weeks after birth (sometimes much earlier, even as early as two to three days after birth). When the foal starts nibbling and even eating the mare's feed, it is important that this be observed, and that the mare not be allowed to have a high starch diet that could affect the foal's gastrointestinal function, which could in turn lead to a lowering of the pH, increasing acidity in the stomach and damaging the intestinal mucosa, resulting in gastric ulcers. Amazingly, the incidence of gastric ulcers in foals at three to four weeks after birth have been shown to be as high as approximately fifty percent.

The early management of the foal's nutritional intake will determine the later status of its gastrointestinal tract, and the balance of the protective and the invasive factors of the intestines will similarly determine the health and the maturation process of the gut. Maintenance of the mucosal bloodflow is one of the most critical and important protective factors. The gut wall of horses have a number of minute finger-shaped processes of the mucous membrane called villi that serve in the absorption of nutriments, with crypts located between adjacent villi. Proper nutritional uptake, the height of the villi, and increased mucosal bloodflow are all related, and reduced mucosal bloodflow will result in shortened villi and shallower crypts, which in turn results in a decreased level of nutritional uptake.

Other important factors that determine the health and the maturation process of the gut are the bicarbonate and mucous production, and the growth and the restitution of the epithelium of the foal's stomach. The bloodflow that delivers vital nutrients and oxygen to the intestinal membrane also takes away invasive products such as hydrogen ions and toxins. Other invasive products are digestion products such as gastric juices, enzymes, and bile salts, all of which are necessary in the normal digestion process, but which if present in excess can cause problems and can damage the intestinal wall.

It is accordingly the primary objective of the nutritional product of the present invention that it both enhance growth and strengthen the immune system in equine foals and, potentially, in other animals and even humans as well. As such, it is an objective of the nutritional product of the present invention that it be useable as either a complement to or substitute for mare's milk. It is a related objective that it promote cell maturation and support nutrient uptake during growth periods, as well as aid in gut maturation and ensure the health and growth of a foal or young horse. It is a further related objective that it help carry and increase the bioavailability of nutrients and help produce required micronutrients.

The other principal objective of the nutritional product of the present invention is that it strengthen the immune system. It is a related objective that it help protect the intestinal mucosa from aggressive actions of potentially dangerous substances and pathogens. It is a further related objective that the nutritional product of the present invention activate protective macrophages to fight infections and increase the immune system, and that it scavenge free radicals that could damage cell tissue and reduce cell immunity. It is a still further objective of the present invention that it protect intestinal tissue, rebuild damaged tissue after chronic diarrhea, and prevent the diarrhea condition and its resulting damage to intestinal tissue.

It is a further objective of the nutritional product of the present invention that it efficaciously treat and prevent digestive tract ulcers in foals and, potentially, in other animals and even humans as well. It is an additional objective of the nutritional product of the present invention that it consist entirely of safe and natural ingredients rather than drugs. It is a still further objective of the nutritional product of the present invention that it be orally administrable, thereby making its dispensation a simple matter.

The nutritional product of the present invention must also be both stable and have a commercially acceptable shelf life, and it should also require no special care to be provided by the user throughout its shelf life prior to usage. In order to enhance the market appeal of the nutritional product of the present invention, it should also be relatively inexpensive when compared to previously known nutritional products for foals to thereby afford it the broadest possible market. Finally, it is also an objective that all of the aforesaid advantages and objectives of the nutritional product of the present invention and its method of administration be achieved without incurring any substantial relative disadvantage.

SUMMARY OF THE INVENTION

The disadvantages and limitations of the background art discussed above are overcome by the present invention. With this invention, a novel nutritional product that is specifically formulated to enhance growth and strengthen the immune system in equine foals is provided. Through the administration of this nutritional product to foals, nutritional uptake, and hence growth and maturation, is optimized, as well as increasing the immune system and protecting against a number of conditions affecting the health of the foal. As will rapidly become apparent to those skilled in the art, the nutritional product of the present invention is more than the sum of its ingredients, with the combination of ingredients yielding a synergistic result more efficacious than the results which would be produced if each of the ingredients acting by itself were provided to foals or other animals.

In its basic form, the nutritional product of the present invention is targeted to accomplish a number of goals, each of which is facilitated by the inclusion of a particular ingredient or a mixture of ingredients in the nutritional product. The first goal of the nutritional product of the present invention is to enhance growth and strengthen the immune system.

The ingredient of the nutritional product of the present invention performs this first goal is a nutricine, and specifically is nucleotides. Nucleotides, which are abundant in colostrum, are vital components to most metabolic functions, since they control the regulatory pathways in growth and provide immunity to diseases. A lack of dietary nucleotides will restrict both the growth and thickness of the intestinal wall. Nucleotides are particularly important in the development of young animals, since nucleotides promote cell maturation and supports nutrient uptake during growth periods. Dietary nucleotides are also critical during and after disease or tissue injury, helping to rebuild damaged tissue such as, for example, after chronic diarrhea. Additionally, nucleotides help in the maintenance of the beneficial hindgut microflora and modify the composition of the microflora positively, thus helping to prevent diarrhea and the resulting damage to intestinal tissue. The nucleotides will also help in recovery after weight loss caused by disease or protein deprivation due to sickness.

The second goal is to provide a high quality protein supplement, which preferably is a kind of protein supplement which also enhances growth and strengthens the immune system. The ingredient of the nutritional product of the present invention performs this second goal is whey protein concentrate, which contains high levels of immunoglobulins and lactalalbumins, both of which proteins are vital in a foal's diet for maintaining a high level of immunity. Protein whey supplement also contains lactoferrin, a valuable protein which also acts as a bacteriostatic and bactericidal agent.

Whey protein concentrate contains high quality proteins and is highly digestible, and will both enhance the live weight gain in a foal and increase its immune defense. In addition, unabsorbed immunoglobulins in the foal's gut will play an important part in protection against intestinal diseases over along period of time after birth. In the preferred embodiment, the whey protein concentrate used is an ultrafiltrate which has not been exposed to high temperature treatment that could destroy these vital proteins.

The third goal also enhances growth and strengthens the immune system. The ingredient of the nutritional product of the present invention which performs this function is a polar lipid supplement. In the preferred embodiment, the polar lipid supplement is oat oil, which contains a high concentration of polar lipids and antioxidants. Optionally, different phases of oat oils may be used in order to vary the characteristics of the oat oil.

The fourth goal of the nutritional product of the present invention is to fight infections and increase the immune system, and to help produce micronutrients. The ingredient of the nutritional product of the present invention which performs this function is a soluble fiber. In the preferred embodiment, β-glucan (beta-glucan), which is the soluble fiber in oats and yeasts, is used as this ingredient. β-glucan is an oligosaccharide that is found in the kernel of oats, and is a powder when dried. β-glucan stabilizes blood sugar and reduces the dangerous cholesterol fraction in the blood. It also activates the protective macrophages to fight infections and increase the immune system. β-glucan is a nutrient for the beneficial bacteria of the hindgut, and helps the bacteria produce the micronutrients that are required by the foal. Finally, it is a jelling agent that has an increased jelling effect when exposed to water, and also has a beneficial spreading effect that spreads the nutritional product on the inner surface of the stomach.

The fifth goal of the nutritional product of the present invention is to increase the body's native ability to enhance growth and to strengthen the immune system. In the preferred embodiment, L-glutamine, which is an essential surfactant amino acid, is used as this ingredient. L-glutamine is a naturally produced amino acid that is produced by breaking down a protein. L-glutamine functions to "kick start" the formation of nucleotides, which, as mentioned above, are involved in the production of cell tissue and the maturation of the intestinal mucosa, and are directly involved in the immune processes and the energy systems. A diet deficient in glutamine will most likely also be deficient in nucleotides.

It will be appreciated by those skilled in the art that these ingredients of the nutritional product of the present invention represent a balanced, multifaceted solution to the nutritional problems posed by foals. With this solution, the nutritional product enhances growth and strengthens the immune system, stimulates a foal's ability to enhance growth and/or strengthen the immune system, and also provides basic nutritional requirements to the foal. The nutritional product of the present invention also treats and prevents digestive tract ulcers in foals. It is believed that the nutritional product of the present invention would also have efficacious application to other animals, including humans.

In the preferred embodiment, the nutritional product of the present invention also optionally includes one or more ingredients to enhance nutrition of a foal. Such ingredients may include vitamins and/or mineral supplements. For example, Vitamin E can be added to the supplement, as can various minerals such as Selenium, Copper, Manganese, Zinc, and Chromium. These ingredients contribute to the nutritional product in their capacity as antioxidants and assist in the total nutritional picture.

The combination of the ingredients discussed above in the preparation of the nutritional product of the present invention for foals and young horses will enhance both growth and immunity of the animals, and result in healthy adult animals. The nutritional product complements and compensating for deficiencies in the mare's milk, and also protects from potentially dangerous pathogens in the feedstuffs available in the mare's feed or forage. The nutritional product of the present invention can be administered in any of a number of ways, and may either be added to feed or fed directly as a nutritional product. It is desirable that the foal is given regular doses of the nutritional product, which in the preferred embodiment is daily or twice daily.

The nutritional product of the present invention may be manufactured as a liquid or paste and stored in a gelatin capsule (as a gelcap), which makes for a consistent dosage of the nutritional product. Alternately, it can be manufactured as a paste for oral administration using a dose syringe. Finally, it may be manufactured pelleted together with grass meal and/or Alfalfa meal. The pelleting procedure should be performed at low temperature, preferably not higher than 65 degrees Celsius. The ingredients mentioned above should be approximately twenty percent by weight of the pellet formulation.

Upon disclosure of the nutritional product of the present invention to those skilled in the art, they will immediately appreciate that the nutritional product is much more than merely the sum of its ingredients. The combination of ingredients yields a synergistic result substantially more efficacious than a sum of the results which would be produced if each ingredient by itself was used.

It may therefore be seen that the present invention teaches a nutritional product which both enhances growth and strengthens the immune system in equine foals and, potentially, in other animals and even humans as well. As such, the nutritional product of the present invention is useable as either a complement to or substitute for mare's milk. It promotes cell maturation and supports nutrient uptake during growth periods, as well as aiding in gut maturation and ensuring the health and growth of a foal or young horse. It helps carry and increase the bioavailability of nutrients and help produce required micronutrients.

The nutritional product of the present invention strengthens the immune system, and helps protect the intestinal mucosa from aggressive actions of potentially dangerous substances and pathogens. It activates protective macrophages to fight infections and increase the immune system, and it scavenges free radicals that could damage cell tissue and reduce cell immunity. The nutritional product of the present invention also protects intestinal tissue, rebuilds damaged tissue after chronic diarrhea, and prevents the diarrhea condition and its resulting damage to intestinal tissue.

The nutritional product of the present invention efficaciously treats and prevents digestive tract ulcers in foals and, potentially, in other animals and even humans as well. It consists entirely of safe and natural ingredients rather than drugs. The nutritional product of the present invention is orally administrable, thereby making its dispensation a simple matter.

The nutritional product of the present invention is stable and has a long shelf life, and requires no special care to be provided by the user throughout its shelf life prior to usage. The nutritional product of the present invention is also inexpensive relative to previously known nutritional products for foals, thereby enhancing its market appeal and affording it the broadest possible market. Finally, all of the aforesaid advantages and objectives of the nutritional product of the present invention and its method of administration are achieved without incurring any substantial relative disadvantage.

DESCRIPTION OF THE DRAWINGS

These and other advantages of the present invention are best understood with reference to the drawings, in which:

FIG. 1 is a somewhat schematic drawing of a horse showing the anatomy of the horse's digestive tract.

DETAILED DESCRIPTION OF THE PREFERRED EMBODIMENT

Prior to a discussion of the nutritional product of the present invention and methods of making and administering it, it is helpful to briefly discuss the anatomy of the digestive system of a horse. Referring to the FIGURE, a side view of a horse 20 is illustrated, schematically illustrating the digestive tract of the horse. The digestive tract of the horse 20 may be separated into a foregut, which is indicated generally by the reference numeral 22, and a hindgut, which is indicated generally by the reference numeral 24.

The digestive tract of the horse 20 begins at its mouth 26, and sequentially extends through an esophagus 28 into a stomach 30 and then into a small intestine 32, which together constitute the foregut 22 of the horse 20. The foregut 22 of the horse 20 constitutes approximately thirty-five to forty percent of the relative capacity of the digestive tract of the horse 20.

From the small intestine 32, the digestive tract extends through a cecum 34, a large colon 36, and a small colon 38 which terminates in a rectum 40. These elements of the digestive tract of the horse 20 together constitute the hindgut 24 of the horse 20. The hindgut 24 constitutes approximately sixty to sixty-five percent of the relative capacity of the digestive tract of the horse 20.

In its simplest implementation, the preferred embodiment of the nutritional product of the present invention includes between three and five primary ingredients which are mixed together to manufacture the nutritional product. These ingredients are: 1. a nutricine to enhance growth and strengthen the immune system; 2. a high quality protein supplement which also enhances growth and strengthens the immune system; 3. a polar lipid supplement which provide antioxidants and galactolipids; 4. a soluble fiber to fight infections and increase the immune system and to help produce micronutrients; and 5. a nutricine to increase the body's ability to enhance growth and/or strengthen the immune system. Each of these ingredients will be discussed separately below, together with a description of its preferred composition, alternative compositions, the preferred amount of the composition used in the nutritional product, and the range of the amount of the composition which may be used in the nutritional product. During the following discussion of the ingredients of the nutritional product of the present invention, it will rapidly become apparent to those skilled in the art that the benefits achieved by the nutritional product of the present invention are greater than the sum of the individual benefits of each of the nutritional product's ingredients.

The first primary ingredient of the nutritional product of the present invention is a nutricine to enhance growth and to strengthen the immune system. The nutricine used in the nutritional product is nucleotides, which are building blocks of DNA or RNA consisting of a nitrogenous base, a phosphate molecule, and a sugar molecule (deoxyribose in DNA and ribose in RNA). Depending upon the sugar, the nucleotides are called deoxyribonucleotides or ribonucleotides. Thousands of nucleotides are linked to form a DNA or RNA molecule. Nucleotides are vital components which are essential for most metabolic functions, since nucleotides control the regulatory pathways in growth and immunity towards diseases.

A lack of nucleotides in a foal's diet will restrict both the growth and the thickness of the intestinal wall of the foal. Thus, nucleotides perform an important function in growth and development of foals, since they promote cell maturation and support nutrient uptake during growth periods of the foal. Dietary nucleotides are also critical during and after disease or tissue injury, and help to rebuild damaged tissue, such as, for example, after chronic diarrhea. Importantly, nucleotides will also help to prevent the diarrhea condition that occurs in young foals.

There are several sources for nucleotides, the best of which are derived from brewer's or baker's yeast. Two sources of products containing nucleotides are S.I. Lesaffre of Cedex, France, and Alltech, Inc. of Nicholasville, Ky. The Lesaffre product is called Yeast Cell Extract (2006), and contains approximately fifteen percent nucleotides. The Alltech product is called NuPro, and contains between five and seven percent nucleotides. Generally, products having higher nucleotide levels are preferred over products having lower nucleotide levels.

The second primary ingredient of the nutritional product of the present invention is a high quality protein supplement which also enhances growth and strengthens the immune system. The protein supplement used in the nutritional product is whey protein concentrate, which is the product resulting from the ultrafiltration of raw liquid whey and its subsequent evaporation and spray drying to a powder. Whey protein concentrate contains high levels of immunoglobulins (IgG) and lactalalbumins, both proteins which are vital in foal's diet in order to maintain a high level of immunity. Protein whey supplement also contains lactoferrin, a protein which has significant effects on the immune system, including acting as a bacteriostatic and bactericidal agent.

In addition to increasing the immune defense, whey protein concentrate is highly digestible and contains high quality proteins which will enhance the live weight gain in the a foal. Unabsorbed immunoglobulins in the foal's gut play an important part in protection against intestinal diseases over along period of time post partum. An advantage of whey protein concentrate over other protein concentrates is that whey protein concentrate is an ultrafiltrate and generally has not been exposed to any high temperature treatment that could destroy these vital proteins.

There are a large number of sources for whey protein concentrate, one example of which is the Volactive Functional Food Products division of Volac International Ltd., of Hertforshire, U.K., which sells whey protein concentrate under the IMUNOPRO name. Whey protein concentrate produced by an ultrafiltration technique is preferred, and the whey protein concentrate must be manufactured at temperatures below 56 degrees Celsius in order to prevent the degradation or destruction of the beneficial ingredients discussed above.

The third primary ingredient of the nutritional product of the present invention is a polar lipid supplement which provide antioxidants and galactolipids. Antioxidants can scavenge the dangerous free radicals that damage cell tissue and reduce the cell immunity. Galactolipids are polar lipids (membrane lipids) that protect intestinal tissue and help carry and increase the bioavailability of nutrients (such as nucleotides and functional proteins (immunoglobulins and lactoalbumins)) to the body. Thus, it is desirable to have a polar lipid supplement which is high in both antioxidants and galactolipids.

There are a number of potential sources of polar lipids that may be used to provide antioxidants and galactolipids in the nutritional product of the present invention. In the preferred embodiment, oat oil is used due to the fact that oat oil has more polar lipids per unit volume than any other any other polar lipid source. Oat oil is also an excellent source of antioxidants. While other oils, especially those containing phospholipids, can be used instead of oat oil, the galactolipids found in plant material are more versatile than the phospholipids and are thus preferred. Other oils that are also good sources of polar lipids are soybean oil, olive oil, palm oil, sunflower oil, corn oil, rapeseed oil, linseed oil, etc.

In the preferred embodiment of the nutritional product of the present invention, the polar lipid supplement is made of different viscosity components of oat oil (or other polar lipid ingredients) in order to affect the ultimate character of the nutritional product. Like most oils, oat oil may come from multiple extractions, with the typical extraction process crushing the oats and treating them with an extraction agent such as hexanol. The first phase of oat oil extracted is a thin oil. The second phase of oat oil extracted is a thick oil, which is considerably more viscous than the first phase. The third phase of oat oil extracted is a very thick oil that has the consistency of grease. All three phases of the oat oil extraction process may be mixed, with the resulting mixture being referred to herein as oat oil. While there are a variety of sources for oat oil, one commercial source for the oat oil is Swedish Oat Fiber AB in Gothenburg, Sweden, which manufactures a high grade of oat oil.

The fourth primary ingredient of the nutritional product of the present invention is a soluble fiber to fight infections and increase the immune system and to help produce micronutrients. The soluble fiber used is an oligosaccharide (a soluble fiber) that is found in oats and yeasts, and which stabilizes blood sugar and reduces the dangerous cholesterol fraction in the blood. This soluble fiber also activates the protective macrophages to fight infections and thereby increase the immune system. It is a nutrient for the beneficial bacteria of the hindgut, helping the bacteria produce the micronutrients that are required by the host body.

There are a number of potential sources of soluble fiber that may be used in the nutritional product in the nutritional product of the present invention. In the preferred embodiment, the soluble fiber used is β-glucan (beta-glucan) that is derived from oats. Other soluble fibers that are also good sources of β-glucan are those derived from barley or soybeans. β-glucan is widely available from a large number of different suppliers, and is a powder when dried.

The fifth primary ingredient of the nutritional product of the present invention is a nutricine to increase the body's ability to enhance growth and strengthen the immune system. The function of this nutricine is to "kick start" the formation of nucleotides, which, as mentioned above, are involved in the production of cell tissue and the maturation of the intestinal mucosa, and are directly involved in the immune processes and the energy systems. In the preferred embodiment, the nutricine used as the fifth primary ingredient is amino acid-based, and preferably is L-glutamine, which is a naturally produced amino acid which is produced by breaking down a protein.

L-glutamine is the most abundant amino acid in the bloodstream, and is primarily formed and stored in skeletal muscle and the lungs. L-glutamine also increases growth hormones, and when ingested has a substantial effect on maintaining and increasing mucosal integrity. L-glutamine is widely available from a large number of different suppliers, and is also a powder.

The pH of the nutritional product of the present invention generally does not need to adjusted, so there is no need for a pH balancer like sodium bicarbonate to be added to the nutritional product.

These five principal ingredients of the nutritional product of the present invention thus enhance growth, strengthen the immune system, provide high quality protein nutrition, antioxidants, and galactolipids, and stimulates the ability to enhance growth and strengthen the immune system. While in the preferred embodiment all five principal ingredients are present in the nutritional product of the present invention, the first three ingredients are viewed as the most important and could be used in a three-ingredient nutritional product. In addition to the five principal ingredients, in the preferred embodiment additional ingredients may be included in the nutritional product of the present invention to further enhance its capacities.

A sixth ingredient which can optionally be added to the nutritional product of the present invention is Yeast Cell Wall, which comprises one or more nutricines which are designed to absorb and eliminate mycotoxins and/or pathogens (i.e., bacteria) in the hindgut (the intestines and the colon). One of the additional ingredients which is made from Yeast Cell Wall and used in the preferred embodiment is a mycotoxin absorbent nutricine that absorbs or soaks up mycotoxins in the hindgut. Another additional ingredient which is made from Yeast Cell Wall and used in the preferred embodiment is a pathogenic bacteria absorbent material that attracts bacteria and passes through the digestive system together with the absorbed pathogenic bacteria in the feces.

The mycotoxin absorbent nutricine used to absorb or soak up mycotoxins in the hindgut is a mycotoxin absorbent material marketed under the registered trademark MYCOSORB by Alltech, Inc. The pathogenic bacteria absorbent material that attracts bacteria and passes through the digestive system together with the absorbed pathogenic bacteria is a pathogenic bacteria absorbent such as the material marketed under the trademark BIOMOS by Alltech, Inc. Another nutricines that could be used instead of MYCOSORB and BIOMOS is the material marketed under the trademark NUTRIMOS (which is essentially a combination of these two Alltech products) by S.I. Lesaffre.

Other additional ingredient(s) of the nutritional product of the present invention are one or more vitamins and minerals which contribute to the final nutritional product in their capacity as antioxidants and/or enhance the total nutritional qualities of the nutritional product. One of the additional ingredients used in the preferred embodiment is Vitamin E. Other additional ingredients used in the preferred embodiment are various minerals such as Selenium, Copper, Manganese, Zinc, and Chromium. In the preferred embodiment these minerals are added in the form of Selenium Yeast, Copper Yeast, Manganese Yeast, Zinc Yeast, and Chromium Yeast, respectively, all of which are available from Alltech, Inc.

Those skilled in the art will immediately appreciate that the nutritional product of the present invention is much more than merely the sum of its ingredients, with the combination of ingredients yielding a synergistic and highly efficacious result.

The relative ranges of amounts of each of the ingredients, and their preferred amounts, will now be discussed, beginning with the nucleotides. The range of amounts of nucleotides is between approximately one-half percent and ten percent of the nutritional product by weight. The preferred amount of nucleotides is approximately five percent of the nutritional product by weight. These percentages are based upon use of the Yeast Cell Extract (2000) from Lesaffre, and will have to be adjusted proportionately upwardly if another Yeast Cell Extract having a lower concentration of nucleotides is used.

The range of amounts of whey protein concentrate is between approximately one-half percent and twenty percent of the nutritional product by weight. The preferred amount of whey protein concentrate is approximately fifty percent of the nutritional product by weight.

The range of amounts of oat oil or other polar lipid supplement is between approximately four percent and fifty percent of the nutritional product by weight. The preferred range of amounts of oat oil or other polar lipid supplement is between approximately twenty-five percent and forty-five percent of the nutritional product by weight. The most preferred amount of oat oil or other polar lipid supplement is approximately thirty-five and four-fifths percent of the nutritional product by weight.

The range of amounts of β-glucan or other soluble fiber is between approximately one-half percent and fifty percent of the nutritional product by weight. The preferred range of amounts of β-glucan or other soluble fiber is between approximately two percent and ten percent of the nutritional product by weight. The most preferred amount of β-glucan or other soluble fiber is approximately two and one-half percent of the nutritional product by weight.

The range of amounts of Yeast Cell Wall is between approximately one-half percent and six percent of the nutritional product by weight. The preferred amount of Yeast Cell Wall is approximately two percent of the nutritional product by weight.

The range of amounts of Vitamin E is between approximately one-twentieth percent and one-half percent of the nutritional product by weight. The preferred amount of Vitamin E is approximately two-tenths percent of the nutritional product by weight.

The range of amounts of each of the selenium yeast, the copper yeast, the manganese yeast, the zinc yeast, and the chromium yeast is between approximately one-twentieth percent and one-tenth percent of the nutritional product by weight. The preferred amount of each of the selenium yeast, the copper yeast, the manganese yeast, the zinc yeast, and the chromium yeast is approximately one-tenth percent of the nutritional product by weight.

The nutritional product of the present invention may be administered either by adding it to feed or by feeding it directly as a nutritional product. In the preferred embodiment, the nutritional product is administered once or twice daily. It may be manufactured either as a liquid, in which case it can be added to feed which is then fed to a horse, or as a liquid or paste and stored in a gelatin capsule (as gelcaps), which makes for a consistent and uniform dosage of the nutritional product. If manufactured as a paste, it can also be orally administered using a dose syringe.

Alternatively, the nutritional product of the present invention may be manufactured by pelleting it together with grass meal and/or Alfalfa meal. The pelleting procedure should be performed at low temperature, preferably not higher than 65 degrees Celsius, to avoid the degradation or destruction of the beneficial ingredients, particularly those contained in the whey protein concentrate. The ingredients of the nutritional product should be approximately twenty percent by weight of the total weight of the pellets.

The preferred dosage of the nutritional product of the present invention is approximately ten grams per day for foals from birth to three months old, approximately twenty grams per day for foals from three months to six months old, and approximately forty grams per day for foals from six months to a year old.

It will be readily apparent to those skilled in the art from the preceding discussion of the ingredients of the nutritional product of the present invention and their interaction that the benefits achieved by the nutritional product of the present invention is substantially greater than the sum of the benefits of each of the nutritional product's ingredients separately.

It may therefore be appreciated from the above detailed description of the preferred embodiment of the present invention that it teaches a nutritional product which both enhances growth and strengthens the immune system in equine foals and, potentially, in other animals and even humans as well. As such, the nutritional product of the present invention is useable as either a complement to or substitute for mare's milk. It promotes cell maturation and supports nutrient uptake during growth periods, as well as aiding in gut maturation and ensuring the health and growth of a foal or young horse. It helps carry and increase the bioavailability of nutrients and help produce required micronutrients.

The nutritional product of the present invention strengthens the immune system, and helps protect the intestinal mucosa from aggressive actions of potentially dangerous substances and pathogens. It activates protective macrophages to fight infections and increase the immune system, and it scavenges free radicals that could damage cell tissue and reduce cell immunity. The nutritional product of the present invention also protects intestinal tissue, rebuilds damaged tissue after chronic diarrhea, and prevents the diarrhea condition and its resulting damage to intestinal tissue.

The nutritional product of the present invention efficaciously treats and prevents digestive tract ulcers in foals and, potentially, in other animals and even humans as well. It consists entirely of safe and natural ingredients rather than drugs. The nutritional product of the present invention is orally administrable, thereby making its dispensation a simple matter.

The nutritional product of the present invention is stable and has a long shelf life, and requires no special care to be provided by the user throughout its shelf life prior to usage. The nutritional product of the present invention is also inexpensive relative to previously known nutritional products for foals, thereby enhancing its market appeal and affording it the broadest possible market. Finally, all of the aforesaid advantages and objectives of the nutritional product of the present invention and its method of administration are achieved without incurring any substantial relative disadvantage.

Although the foregoing description of the nutritional product of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A nutritional product for equine foals, comprising:
 a polar lipid that has been isolated from its natural source which polar lipid is high in galactolipids and antioxidants;
 a soluble fiber source that has been fractionated from its natural origin which soluble fiber source exerts a beneficial effect on health, wherein said soluble fiber source is derived from at least one ingredient selected from the group consisting of oats, barley, and soybeans;
 a nutricine consisting of a source of dietary nucleotides; and
 a protein concentrate;
wherein said polar lipid, said soluble fiber source, said nutricine, and said protein concentrate are present in said nutritional product in respective amounts sufficient to enhance growth and/or strengthen the immune system of equine foals.

2. A nutritional product as defined in claim 1, wherein said polar lipid contains antioxidants.

3. A nutritional product as defined in claim 1, wherein said polar lipid contains lipids of oats.

4. A nutritional product as defined in claim 1, wherein said polar lipid comprises at least one oil selected from the group consisting of oat oil, soybean oil, olive oil, palm oil, sunflower oil, corn oil, rape seed oil, and linseed oil.

5. A nutritional product as defined in claim 1, wherein said polar lipid comprises:
 oat oil.

6. A nutritional product as defined in claim 5, wherein said oat oil comprises a mixture of oat oil from all phases of the extraction process.

7. A nutritional product as defined in claim 1, wherein said polar lipid comprises between approximately four percent and fifty percent of said nutritional product by weight.

8. A nutritional product as defined in claim 7, wherein said polar lipid comprises between approximately twenty-five percent and forty-five percent of said nutritional product by weight.

9. A nutritional product as defined in claim 8, wherein said polar lipid comprises approximately thirty-five and four-fifths percent of said nutritional product by weight.

10. A nutritional product as defined in claim 1, wherein said soluble fiber source is an oligosaccharide.

11. A nutritional product as defined in claim 1, wherein said soluble fiber source is derived from oats.

12. A nutritional product as defined in claim 1, wherein said soluble fiber source comprises:
 β-glucan (beta-glucan).

13. A nutritional product as defined in claim 12, wherein said wherein said β-glucan is derived from oats.

14. A nutritional product as defined in claim 1, wherein said soluble fiber source comprises between approximately one-half and fifty percent of said nutritional product by weight.

15. A nutritional product as defined in claim 14, wherein said soluble fiber source comprises between approximately two and ten percent of said nutritional product by weight.

16. A nutritional product as defined in claim 15, wherein said soluble fiber source comprises approximately two and one-half percent of said nutritional product by weight.

17. A nutritional product as defined in claim 1, wherein said source of dietary nucleotides comprises:
 yeast cell extract.

18. A nutritional product as defined in claim 17, wherein said yeast cell extract comprises between approximately one-half percent and ten percent of said nutritional product by weight.

19. A nutritional product as defined in claim 18, wherein said yeast cell extract comprises approximately five percent of said nutritional product by weight.

20. A nutritional product as defined in claim 17, wherein said yeast cell extract is derived from bakers or brewers yeast.

21. A nutritional product as defined in claim 1, wherein said nutricine additionally comprises:
 yeast cell wall.

22. A nutritional product as defined in claim 21, wherein said yeast cell wall comprises between approximately one-half percent and five percent of said nutritional product by weight.

23. A nutritional product as defined in claim 22, wherein said yeast cell wall comprises approximately two percent of said nutritional product by weight.

24. A nutritional product as defined in claim 1, wherein said protein concentrate comprises:
 whey protein concentrate.

25. A nutritional product as defined in claim 24, wherein said whey protein concentrate contains high levels of immunoglobulins and lactalalbumins.

26. A nutritional product as defined in claim 1, additionally comprising:
 a nutricine which stimulates the formation of nucleotides.

27. A nutritional product as defined in claim 26, wherein said nutricine which stimulates the formation of nucleotides comprises:
 L-glutamine.

28. A nutritional product as defined in claim 27, wherein said L-glutamine comprises between approximately two percent and six percent of said nutritional product by weight.

29. A nutritional product as defined in claim 28, wherein said L-glutamine comprises approximately four percent of said nutritional product by weight.

30. A nutritional product as defined in claim 1, additionally comprising:
 Vitamin E.

31. A nutritional product as defined in claim 30, wherein said Vitamin E comprises approximately two-tenths percent of said nutritional product by weight.

32. A nutritional product as defined in claim 1, additionally comprising:
 at least one mineral micronutritional additive.

33. A nutritional product as defined in claim 32, wherein at least one mineral micronutritional additive comprises:
 one or more from the group consisting of selenium yeast, copper yeast, manganese yeast, zinc yeast, and chromium yeast.

34. A nutritional product as defined in claim 33, wherein each said mineral micronutritional additive comprises approximately one-tenth percent of said nutritional product by weight.

35. A nutritional product as defined in claim 1, additionally comprising:
 a medication that is carried with the other ingredients of said nutritional product, wherein at least one of the absorption or the therapeutic value of said medication is maximized by being taken in conjunction with said nutritional product.

* * * * *